United States Patent [19]

Abber

[11] Patent Number: 4,925,671

[45] Date of Patent: May 15, 1990

[54] SILICONE PRESSURE SENSITIVE ADHESIVE AND USES

[75] Inventor: Herman Abber, Brockton, Mass.

[73] Assignee: Flexcon Company, Inc., Spencer, Mass.

[21] Appl. No.: 865,750

[22] PCT Filed: Jul. 7, 1984

[86] PCT No.: PCT/US84/01068

§ 371 Date: May 5, 1986

§ 102(e) Date: May 5, 1986

[87] PCT Pub. No.: WO86/00532

PCT Pub. Date: Jan. 30, 1986

Related U.S. Application Data

[63] Continuation-in-part of Ser. No. 324,362, Nov. 24, 1981, abandoned.

[51] Int. Cl.$^5$ ............................................. A61F 13/02
[52] U.S. Cl. .................................... 424/448; 424/449; 525/477
[58] Field of Search ......................... 424/448; 525/477

[56] References Cited

U.S. PATENT DOCUMENTS

| | | | |
|---|---|---|---|
| 2,857,356 | 10/1958 | Goodwin | 428/268 |
| 3,598,122 | 8/1971 | Zaffaroni | 424/448 |
| 3,652,475 | 3/1972 | Wade et al. | 525/477 |
| 4,016,328 | 4/1977 | Horning | 525/477 |
| 4,039,707 | 8/1977 | O'Malley | 428/40 |

Primary Examiner—Thurman K. Page
Assistant Examiner—L. R. Horne
Attorney, Agent, or Firm—George E. Kersey

[57] ABSTRACT

Pressure sensitive adhesive having favorable adhesive, shear, liquid permeability, and release characteristics. The adhesive is a crosslinked polymerization product of a methyl/phenyl siloxane gum, dimethyl siloxane gum and a polysiloxane resin. The resulting product provides suitable adhesion to a large number of surfaces and has particular utility as an adhesive between plastic film and human skin, especially for use with transdermal therapeutic devices. The adhesive characteristic mitigates damage to underlying surfaces such as human skin tissue during adhesive removal.

7 Claims, No Drawings

SILICONE PRESSURE SENSITIVE ADHESIVE AND USES

This application is a continuation in part of patent application Ser. No. 324,362 filed Nov. 24, 1981, now abandoned.

BACKGROUND OF THE INVENTION

1. Field of the Invention

The present invention relates to pressure sensitive adhesives which provide suitable adherence of objects to the human skin. The invention relates more particularly to silicone based pressure sensitive adhesives which are of particular use in transdermal therapeutic devices for attachment to the human skin.

2. Description of the Prior Art

Pressure sensitive adhesives for use on human skin are used typically in bandages or other therapeutic devices which must adhere to the skin for a prescribed period of time. Such devices are typically comprised of a plastic or cloth film layer coated with a pressure sensitive adhesive. The pressure sensitive adhesive is protected with a release substrate which is readily peelable from the adhesive coating. The pressure sensitive adhesive for use in connection with such bandages or other therapeutic device must satisfy an array of specific physical characteristics. Importantly the release substrate must be easily peelable from the adhesive coating and the adhesive must have sufficient cohesion to keep the bandage or therapeutic object in adhesive contact with the skin for a prescribed period of time. Also the adhesive must not cause skin inflammation and must be nontoxic.

Additionally a pressure sensitive adhesive as applied to a transdermal therapeutic device must meet other strict performance requirements. A transdermal device is a medicinal pouch which contains a liquid medicine or other drugs which must be absorbed gradually into the skin over a fairly long period of time. These devices typically contain a semipermeable membrane and are advantageously used with drugs which are best absorbed into the human body gradually, such as nitroglycerine or other drugs useful in treating cardiac impairment. Thus, the pressure sensitive adhesive which is coated onto the therapeutic device must not act as a barrier to interrupt the flow of a fluid from the device and into the human blood stream. Specifically, the pressure sensitive adhesive must be permeable to the drug being used. Furthermore, since the therapeutic device must remain in close adhesive contact with the skin over a period of time typically at least up to 24 hours, the adhesive should keep essentially all of the contact surface of the therapeutic device in adhesive contact with the patient's skin over this entire period. The pressure sensitive adhesive should also permit the therapeutic device to be peeled from the skin without causing discomfort and without leaving an adhesive residue on the skin which is not easily removeable.

U.S. Pat. Nos. 2,857,356 and 4,039,707 are illustrative of prior art silicone-based pressure sensitive adhesives. U.S. Pat. No. 2,857,356 discloses a pressure sensitive adhesive formed from the polymerization of a silicate resin and an organopolysiloxane fluid. The silicate resin is obtained by intercondensing a mixture comprising a cohydrolysis product of a trialkyl hydrolyzable silane and an alkyl silicate, said cohydrolysis product containing a plurality of silicone-bonded hydroxy groups. The formulation disclosed in this reference is directed principally to forming a pressure sensitive adhesive which retains a high degree of tack and cohesion over a wide temperature range, for example between about −75° C. and 250° C. The pressure sensitive adhesive product disclosed in this reference is directed to application principally as an adhesive coating for use in contacting polymeric material such as glass, a wide range of plastics such as polyethylyene, and also for use in connection with the manufacture of pressure sensitive tapes. There is no reference made in this disclosure to suitability of the adhesive product for application to human skin. In order to achieve the high degree of tack and cohesive strength, patentees disclose that the weight ratio of the silicate resin to the organopolysiloxane fluid should be between about 0.5/1 to 6/1, more preferably between about 1/1 to 3/1. (Column 7, lines 21 to 28). The range of formulations disclosed in this reference could not be suitable for application to a transdermal therapeutic device because of insufficient tack for application to human skin and too great a time lapse required to achieve maximum bonding.

U.S. Pat. No. 4,039,707 discloses a siloxane-type pressure sensitive adhesive which is composed of the intercondensation product of a mixture containing an organopolysiloxane resin and at least one alkylaryl polysiloxane gum. The organopolysiloxane resin is defined at Column 6, lines 5 to 10 as having the formula:

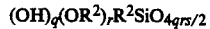

$(OH)_q(OR^2)_r R^2 SiO_{4qrs/2}$

It is also disclosed as essential that the organopolysiloxane gum contain aryl groups, such as phenyl groups, to obtain optimum pressure sensitive adhesive properties. If a mixture of phenyl and methyl groups is employed, this reference teaches that the number of silicone-bonded phenyl groups should be maintained with such a range that for each 2 to 75 phenyl groups attached directly to silicone by a carbon silicone linkage there are present from 98 to 25 silicone-bonded methyl groups, with the preferred range for instance from about 5 to 15 phenyl groups per 95 to 85 methyl groups. (Column 5, line 59 to Column 6, line 2). This reference also discloses a use of a release substrate covering the pressure sensitive adhesive. The release substrate may typically be a paper or polymer film coated with a release coating such as a silanol-stopped dimethylpolysiloxane fluid. Another release coating which is disclosed in this reference is based on dimethylvinyl-stopped dimethyl polysiloxane fluid. Additionally, the reference discloses that the alkylaryl polysiloxane gum should have a viscosity from about 200,000 to 15 million centipoise at 25° C. and contain an average from about 1.85 to 2.01 silicone-bonded alkyl and aryl radicals per silicone atom.

Although use of an alkylaryl polysiloxane gum with an organopolysiloxane resin is disclosed in this reference, the reference does not disclose or suggest use of specific combinations of alkylaryl polysiloxane gums to improve the product's adhesive, shear and liquid permeability characteristics so that the adhesive product may be used with transdermal therapeutic devices.

Accordingly, it is an object of the present invention to provide an improved pressure sensitive adhesive which has particular use as an adhesive for retaining a plastic film or therapeutic device in adhesive contact with the human skin and which adhesive is nontoxic and easily removeable from the skin.

An important object of the invention is to provide a pressure sensitive adhesive for particular use in transdermal therapeutic devices. A related object is to provide pressure sensitive adhesive which retains the therapeutic device in adhesive contact with the human skin over a prolonged period of time and does not interfere with the absorption of medicinal fluid from the transdermal device through the adhesive and into the skin.

SUMMARY OF THE INVENTION

The pressure sensitive adhesive of the invention has been formulated to satisfy an array of specific performance requirements so that the product has a particular suitability for use as a pressure sensitive adhesive for transdermal therapeutic devices which are applied in adhesive contact with the skin. The pressure sensitive adhesive formulation is composed of the combination of a methyl/phenyl siloxane preferably dimethyl diphenyl siloxane gum with a dimethyl siloxane gum and an organopolysiloxane resin. Preferably, the resin is composed of monofunctional and quadrafunctional siloxane units, designated hereinafter as an MQ resin. Applicants have found that such a formulation provides a polymerized pressure sensitive adhesive having the requisite array of performance characteristics for use in connection with transdermal therapeutic devices. A suitable catalyst such as a diaryl peroxide catalyst is advantageously included in the mixture to initiate polymerization between the siloxane gum and resin to form the pressure sensitive adhesive product. Alternatively, the catalyst may be omitted and the polymerization initiated by other means.

Although it is conventional wisdom that dimethyl diphenyl siloxane gum is imcompatible with dimethyl siloxane gum, applicants have found that over a specified range in concentration of these components in the presence of an MQ resin, a pressure sensitive adhesive product can be formed. The resulting adhesive product has an array of specific performance characteristics which make the product particularly suitable for use as a pressure sensitive adhesive for transdermal therapeutic devices. The weight ratio of a dimethyl diphenyl siloxane gum to dimethyl siloxane gum should preferably be in a range between 1/3 to 3/1. In the embodiment including a catalyst, a diaryl peroxide catalyst may be used comprising between about 0.1 to 2 percent by weight of the polymerized pressure sensitive adhesive product. A preferred catalyst of this type is composed of 2, 4, dichloro benzoyl peroxide containing a phlegmatic agent such as dibutylphthalate. The pressure sensitive adhesive formulation may additionally include polybutene resin in an amount of up to approximately 15 percent by weight of the polymerized adhesive product.

An alternative formulation for the polymerized adhesive product of the invention is composed of dimethyl diphenyl siloxane gum, an organopolysiloxane resin (preferably MQ resin), and a suitable catalyst such as a diaryl peroxide catalyst as above described. The catalyst typically should be between about 0.1 to 5 percent by weight of the adhesive product. Although this formulation produces an acceptable product for use in connection with a transdermal therapeutic device, the product exhibits somewhat less satisfactory release characteristics in removing the release substrate from the adhesive as compared with the preferred formulation containing both dimethyl/diphenyl siloxane gum and dimethyl siloxane gum.

The polymerized pressure sensitive adhesive product is preferably prepared by forming a raw adhesive solution composed of the reactants set forth above, and solvents such as toluene, naphtha, xylene and n-butyl acetate. In the alternative formulations polybutene resin may be included, or as above-mentioned, the dimethyl siloxane gum may be omitted from the preferred formulation. The raw adhesive solution is prepared by mixing the siloxane gum, MQ resin, catalyst and solvents until a homogeneous solution is formed. The solution is coated onto a release substrate (typically a paper sheet overcoated with a silicone release coating), thus forming an adhesive laminate. The adhesive laminate is dried to vaporize the solvents after which the laminate is heated to temperatures necessary to initiate a polymerization reaction between the siloxane gum and MQ resin.

The adhesive laminate may be transferred to a surface of a transdermal device so that the adhesive coating comes into direct contact with the device. Preferably, the adhesive coating comes into direct contact with a semipermeable membrane component of the transdermal device. The user need only peel off the release substrate to expose the adhesive layer prior to pressing the transdermal device onto his skin. It has been found that the pressure sensitive adhesive formulation of the invention exhibits unique liquid permeability characteristics and a high degree of adhesion to human skin, yet causes negligible skin irritation or redness and has excellent release properties permitting easy removal of a release substrate from the adhesive.

DETAILED DESCRIPTION

The pressure sensitive adhesive of the invention is preferably composed of the combination of a methyl/phenyl siloxane gum; a dimethyl siloxane gum; an organopolysiloxane resin, advantageously MQ resin; and suitable catalyst. A suitable methyl/phenyl siloxane gum is a dimethyl diphenyl siloxane. The term "gum" as used herein denotes a high viscosity, e.g. greater than about 20,000 centipoise, linear alkyl/aryl polysiloxane or polydiorganosiloxane that can be converted from a highly viscous plastic state into the predominantly elastic state by crosslinking. See, W. Noll, "Chemistry and Technology of Silicones", *Academic Press*, New York (1958), p. 387. The term "organosiloxane elastomer" is hereinafter defined as synonymous and interchangeable with the term "gum" as above-defined. See. W. Noll, supra, p. 387. The term "resin" as used in this patent application is synonymous with "polymer". The pressure sensitive adhesive is particularly useful for attaching a transdermal therapeutic device to human skin for a period of up to about 24 hours. The adhesive exhibits favorable peel release characteristics and a high degree of adhesion over a prolonged period. The adhesive is particularly suited to medical applications in that it is easily removed from the skin and nonirritating, and permits the medication in the transdermal device to pass from the device, through the adhesive, and thence into the skin.

Transdermal devices are well known in the art. They are composed of a semipermeable microporous membrane or membranes for storing a supply of liquid medication and causing release of the medication therefrom at constant rate over a prolonged period of time. The transdermal device containing the liquid medication is applied directly to the skin in the form of a bandage. The semipermeable membrane in contact with the skin must be provided with a pressure sensitive adhesive layer in order to adhere to the skin. The reference U.S. Pat. Nos. 4,200,093 and 4,201,211 are merely representative of transdermal therapeutic devices to which the adhesive of the invention is applicable. The adhesive of the invention has general applicability to essentially any transdermal device which must be adhesively placed in contact with the skin, and therefore the invention is not intended to be limited to the foregoing references but rather is incorporated by references herein merely for illustrative purposes.

A suitable adhesive for transdermal therapeutic devices should satisfy a number of specific requirements. The adhesive must allow the liquid medicine to flow uninterrupted over a prolonged period of time, e.g. up to at least 6 hours and preferably up to at least 24 to 36 hours and longer, at constant rate, through the semipermeable membrane and into the skin. Therefore, the adhesive cannot form a barrier between the membrane and the skin during the required prolonged period of use so as to measurably retard the constant rate of flow of the medicine from the membrane into the human skin. It has been found that the adhesive formulation of the invention satisfies all the aforesaid requirements, whereas conventional pressure sensitive adhesives have been found to significantly retard the free flow of liquids therethrough, especially over a prolonged period.

Additionally, the adhesive should not cause undue irritation to the skin, including swelling, redness or itching on prolonged contact (typically up to at least 24 hours). The adhesive should also allow for relatively easy removal of the transdermal device from the skin without causing great discomfort to the patient. In order to provide a suitable adhesive for use with a transdermal device, the adhesive should not significantly deteriorate in strength or tend to peel or loosen over the 24 hour period. Additionally, there should be very little or no adhesive residue remaining on the skin after the transdermal device is peeled from the skin.

A pressure sensitive adhesive formulation which has been found to satisfy the above requirements is presented as formulation A in Table I. The pressure sensitive adhesive formulation A is composed of a raw adhesive solution which is dried to evaporate the solvents and then cured to form the polymerized pressure sensitive adhesive product A, having a composition shown in Table I.

Raw adhesive solution A as shown in Table I is composed of a methyl/phenyl siloxane gum such as dimethyl diphenyl siloxane gum, and organopolysiloxane resin, preferably MQ resin, dimethyl siloxane gum, suitable catalysts and solvents. The methyl/phenyl siloxane gum such as dimethyl diphenyl siloxane gum as well as the dimethyl siloxane gum may typically have a viscosity between about 20,000 and 10,000,000 centipoise at 25° C., preferably between about 20,000 and 1,000,000 centipoise at 25° C. The MQ resin included in formulation A is composed of monofunctional and quadrofunctional siloxane units and has the generic chemical formula: $M_xQ_y$, where $M=R_3SiO_{1/2}$; $Q=SiO_{4/2}$; and R preferably is a methyl group. However, R may include any other alkyl group particularly $C_1$ to $C_4$ alkyl groups, i.e. methyl, ethyl, propyl and butyl alkyl groups.

The molar ratio of phenyl groups to methyl groups in the dimethyl diphenyl siloxane gum is at least about 0.1/1 and preferably between about 0.1/1 and 0.2/1. Mixtures of dimethyl diphenyl siloxane gum and suitable MQ resin may be purchased under the tradename SILGRIP SR6574 manufactured by the General Electric Company of Waterford, N.Y. The MQ resin is commercially available in dry powdery particulate form. A preferred MQ resin to be added to this mixture is commercially available under the tradename CR542 from General Electric Company. Another MQ resin suitable for use in adhesive solution A is commercially sold under the tradename C42-2109 designated as a controlled release additive from Dow Corning Co. of Midland, Mich. A suitable mixture of dimethyl siloxane gum and MQ resin is available under the trade designation 280 A adhesive from Dow Corning Co.

The preferred catalyst is a diaryl peroxide type catalyst, such as that containing 2, 4, dichloro benzoyl peroxide, which contains a phlegmatic agent such as dibutyl phthalate. A catalyst of this type is available under the tradename CADOX TDP, available from Noury Chemical Company of Burt, N.Y. The raw adhesive solution A as set forth in Table I further contains solvents, preferably toluene, naphtha, xylene, and n-butyl acetate in the proportions listed.

An alternate pressure sensitive adhesive formulation B is tabulated in Table II. This formulation has also been found to satisfy the above-referenced requirements. The pressure sensitive adhesive formulation B is composed of a raw adhesive solution which is dried to evaporate the solvents contained therein and then cured to form the polymerized pressure sensitive adhesive product B having a composition shown in Table II.

The composition of formulation B is similar to that of formulation A except that a small amount of polybutene resin was found to be desirable because it produced greater tack and somewhat better adhesion. A suitable polybutene resin is available under the tradename INDOPOL (medium molecular weight) available from Amoco Company of Chicago, Ill. The MQ resin included in formulation B has the generic formula $M_xQ_y$ where $M=R_3SiO_{1/2}$, $Q=SiO_{4/2}$; and R preferably is a methyl group. However, R may be composed of any other alkyl group, particularly $C_1$ to $C_4$ alkyl groups such as methyl, ethyl, propyl and butyl alkyl groups. The dimethyl diphenyl polysiloxane gum included in raw adhesive solution B preferably has a molar ratio of phenyl groups to methyl groups at least about 0.1/1 and preferably between about 0.1/1 to 0.2/1.

A preferred formulation containing both dimethyl diphenyl siloxane gum and MQ resin for use in adhesive solution B is SILGRIP SR6574, available from the General Electric Company. A preferred MQ resin to be added to adhesive solution B is available under the tradename CR542 from General Electric Company. Another MQ resin suitable for use in adhesive solution B is sold under the tradename C42-2109 from Dow Corning Co. A preferred formulation containing both dimethyl siloxane gum and MQ resin for use in adhesive solution B may be purchased under the tradename 280 A adhesive from Dow Corning Company.

A suitable catalyst for formulation B is a diaryl peroxide type catalyst, such as that containing 2, 4 dichloro benzoyl peroxide which contains a phlegmatic agent such as dibutyl phthalate. A catalyst of this type may be purchased under the tradename CADOX TDP from Noury Chemical Company. The raw adhesive solution as set forth in Table II further contains solvents toluene, naphtha, xylene and n-butyl acetate in the proportions listed.

Although the preferred catalyst shown in Tables I and II is a diaryl peroxide, such as 2, 4, dichloro benzoyl peroxide, other catalysts may be employed. Other catalysts include, for example, diacyl peroxide; amino silanes; secondary or tertiary amines; or an organic titanate such as terabutyl titanate available under the tradename TYZOR TBT from DuPont Company of Wilmington, Del. Alternatively, the catalyst may be omitted and the polymerization reaction initiated by other means such as electron beam contact.

Although the solvents listed in Tables I and II are most desirable, other solvents may be used, such as, for example toluene, naphtha and esters such as ethyl acetate and butyl acetate.

Although dimethyl diphenyl polysiloxane gum is preferred any methyl/phenyl polysiloxane gum may be used. Preferably, the methyl/phenyl polysiloxane gum has a molar ratio of phenyl groups to methyl groups between about 0.1/1 and 0.2/1. When employing as a basic ingredient one of the gum/resin mixtures recited above, the polymerized pressure sensitive adhesive product advantageously includes between about 0.1 to 15 weight percent of additional MQ resin and between about 0.1 to 2.0 weight percent catalyst. Typically the weight ratio of methyl/phenyl siloxane gum to dimethyl siloxane gum is in a range between about 1/3 to about 3/1 although a weight ratio approaching 3/1 is preferred.

Either of the adhesive solutions A or B may be made by mixing the constituents listed in Table I in a conventional closed mixing vat until a homogeneous solution is achieved. Although the various components may be added in any order, it is advantageous to premix the catalyst and solvents followed by addition of the remaining components. The homogeneous raw solution is then coated onto a release substrate, typically composed of a paper sheet overcoated with a release coating such as conventional silicone release fluids; e.g. polydimethylvinyl siloxane fluid containing appropriate catalysts such as one containing a noble metal complex. The overcoated release substrate forms an adhesive laminate sheet which is then dried, typically in conventional convective driers operating between approximately 100° F. to 200° F., in order to evaporate the solvents contained in the raw adhesive coating. The dried adhesive laminate is then passed through a curing oven operating at a temperature level of between about 200° F. to 350° F., wherein a crosslinking type polymerization reaction occurs between the siloxane gums, the MQ resin, and the catalyst.

The adhesive laminate sheet containing the cured pressure sensitive adhesive product may be transferred directly to a surface of the semipermeable membrane of a transdermal therapeutic device. Transfer may be accomplished by passing the adhesive laminate sheet and the semipermeable membrane film through a conventional laminator. The adhesive coated semipermeable membrane may then be cut into desired shapes for use in manufacture of transdermal therapeutic devices. In use of the transdermal device, the patient will peel off the release substrate portion of the adhesive laminate sheet thus exposing the adhesive coated semipermeable membrane so that direct contact can be made between the adhesive coated semipermeable membrane and the human skin.

Various performance tests for the polymerized pressure sensitive adhesive product were made for formulations tabulated in Table I and II. The results of the performance tests are tabulated in Table III.

TABLE I

| Pressure Sensitive Adhesive (P.S.A.) - Formulation A | |
|---|---|
| Raw Adhesive Solution A | Comp., Wt. % |
| Mixture of Dimethyl Diphenyl Siloxane Gum Plus MQ Resin (e.g. SILGRIP SR 6574) | 36.9 |
| Additional MQ Resin (e.g. CR 542) | 0.5 |
| Mixture of Dimethyl Siloxane Gum Plus MQ Resin (e.g. 280 A Adhesive) | 12.5 |
| Catalyst (e.g. Diaryl Peroxide and Phlegmatic Agent as in CADOX TDP) | 0.2 |
| Solvent 1 Toluene | 15.4 |
| Solvent 2 Naphtha | 15.1 |
| Solvent 3 Xylene | 8.3 |
| Solvent 4 n-Butyl Acetate | 11.1 |
| | 100.0 |

| Polymerized Pressure Sensitive Adhesive Product A | |
|---|---|
| Raw Adhesive Solution A | Comp., Wt. % |
| Mixture of Dimethyl Diphenyl Siloxane Gum Plus MQ Resin (e.g. SILGRIP SR 6574) | 73.6 |
| Additional MQ Resin (e.g. CR 542) | 1.1 |
| Mixture of Dimethyl Siloxane Gum Plus MQ Resin (e.g. 280 A Adhesive) | 24.9 |
| Catalyst (e.g. CADOX TDP) | 0.4 |
| | 100.0 |

TABLE II

| Pressure Sensitive Adhesive (P.S.A.) - Formulation B | |
|---|---|
| Raw Adhesive Solution B | Comp., Wt. % |
| Mixture of Dimethyl Diphenyl Siloxane Gum Plus MQ Resin (e.g. As in SILGRIP 6574) | 34.9 |
| Additional MQ Resin (e.g. CR 542) | 0.9 |
| Mixture of Dimethyl Siloxane Gum Plus MQ Resin (e.g. 280 A Adhesive) | 12.6 |
| Catalyst (e.g. CADOX TDP) | 0.2 |
| Polybutene Resin (e.g. Indopol 300) | 1.7 |
| Solvent 1 Toluene | 14.8 |
| Solvent 2 Naphtha | 14.2 |
| Solvent 3 Xylene | 8.3 |
| Solvent 4 n-Butyl Acetate | 12.4 |
| | 100.0 |

| Polymerized Pressure Sensitive Adhesive Product B | |
|---|---|
| | Comp., Wt. % |
| Mixture of Dimethyl Diphenyl Siloxane Gum and MQ Resin (e.g. SILGRIP 6574) | 69.4 |
| Additional MQ Resin (e.g. CR 542) | 1.8 |
| Mixture of Dimethyl Siloxane Gum and MQ Resin (e.g. 280 A Adhesive) | 25.0 |
| Catalyst (e.g. CADOX TDP) | 0.4 |
| Polybutene Resin (e.g. Indopol 300) | 3.4 |
| | 100.0 |

TABLE III
PERFORMANCE TEST RESULTS

| I. TEST SAMPLE FORMULATIONS | Adhesive Formulation A | Adhesive Formulation B | For Use With Transdermal Therapeutic Devices |
|---|---|---|---|
| Adhesive Thickness Range | 1.3 mil<br>1.0 to 1.7 mil | 2.2 mil<br>1.3 to 3.2 mil | 0.7<br>0.75 to 4.0 |
| II. PERFORMANCE | | | |
| Degree of adhesion after 24 hours[1] | 95 percent | 95 percent | 90 percent |
| Peel adhesion from stainless steel (grams per inch width)[2] | 850 | 990 | 570 |
| Peel adhesion from release substrate (gms. per inch width)[3] | 120 | 50 | 20 |

| TEST SAMPLE FORMULATIONS | Dry Pressure Sens. Adhesive Formulation A | Dry Pressure Sens. Adhesive Formulation B | Minimum Required For Use With Transdermal Therapeutic Devices |
|---|---|---|---|
| Adhesive residue remaining 24 hours after removal of transdermal device from skin[4] | 5 to 10 percent | 5 to 10 percent | Less than 20 |
| Erythema (Irritation to skin) | | | |
| 6 hours | Almost imperceptible redness | Almost imperceptible redness | Barely perceptible redness |
| 24 hours | None | None | Less than perceptible |
| Edema (Swelling or redness) | | | |
| 6 hours | Negligible | Negligible | Negligible |
| 24 hours | Less than 50 percent of occluded area | Less than 50 percent of occluded area | Less than 50 percent of occluded area |
| Itching | Mild | Mild | Mild |
| Permeability to Liquid (nitroglycerin release rate: mg/hr./cm$^2$)[5] | 35 to 40 | 35 to 40 | At least 30 |

[1] The percent of initial adhesive contact area remaining in contact with the skin.
[2] Performed using Pressure Sensitive Tape Council Standard Test No. PSTC-1.
[3] Measured with angle between the release substrate and the semipermeable membrane of ethylene vinyl acetate held at 90°.
[4] Percent of initial adhesive contact area.
[5] Average rate over a period of 27 hours using adhesive of thickness 2.2 ± 0.9

The production of a pressure sensitive adhesive in accordance with the invention is further illustrated by the following nonlimiting example:

EXAMPLE

A batch of raw adhesive solution was prepared in accordance with either of the formulations of Tables I and II. The catalyst was dispersed first into the solvents and the solvents with dispersed catalyst therein were then added to the siloxane gum and MQ resin constituents. Dispersing the catalyst first in the solvents reduced the mixing time required to achieve a homogeneous solution. After the raw adhesive solution had been formed in accordance with the formulation shown in Table I the solution was mixed within a closed sealed drum with a high speed air driven agitating mixer.

The mixing was continued under ambient conditions until a homogeneous raw adhesive solution was obtained. The raw adhesive solution was then coated onto a release substrate which was composed of a paper sheet precoated with a polydimethylvinyl siloxane fluid with the noble metal complex catalyst 7048 of Dow Corning Co. The raw adhesive was coated onto the release substrate using conventional three roll reverse rollers to achieve a coating thickness of about 3.5 mils. The release substrate coated with the raw adhesive solution formed an adhesive laminate sheet.

The adhesive laminate sheet was then passed through a conventional convective coater drier, operated under four temperature zones. The first zone included temperatures between about 80° to 125° F.; the second zone between about 125° to 200° F.; the third zone between about 200° to 250° F. and the fourth zone at about 350° F. The adhesive laminate sheet passed continuously through the convective drier at about 40 feet per minute. The total length of the four zones was about 100 feet. As the adhesive laminate passed through the first two zones of the convective oven, the solvents evaporated from the raw adhesive solution which was coated onto the release substrate. Then as the adhesive laminate continued through zones 3 and 4, i.e., the curing zones, cross-linking polymerization reaction occurred forming the polymerized pressure sensitive adhesive product.

The adhesive laminate sheet containing the polymerized pressure sensitive adhesive coating was transferred onto a surface of a semipermeable membrane for use within a transdermal therapeutic device of which U.S. Pat. Nos. 4,200,098 and 4,201,211 are merely illustrative. A conventional laminator was used to transfer the adhesive laminate onto the surface of the semipermeable membrane. The semipermeable membrane sheet with the attached adhesive laminate was then cut in predesignated shapes or stored in rolls for use in connection with the manufacture of transdermal therapeutic devices.

It will be appreciated that other formulations for the pressure sensitive adhesive product may be prepared in a manner similar to that set forth above without departing from the spirit and scope of the invention.

What is claimed is:

1. A combination of a medical device to be placed in adhesive contact with the skin and a pressure sensitive adhesive at least partially coated on said device, the adhesive permitting passage of medicinal liquids therethrough, said adhesive comprising a mixture of nitroglycerin and:
   the polymerization product of a mixture of reactants comprised of a linear methyl/phenyl polysiloxane gum,
   a linear dimethyl polysiloxane gum, and
   an MQ organopolysiloxane comprising monofunctional and quadrifunctional siloxane units,
   the adhesive permitting passage of nitroglycerin therethrough at substantially constant rate of at least 30 mg./hr./cm$^2$ as measured over a 27-hour period with the adhesive having a thickness of about 2.2±0.9 mil.

2. The combination of claim 1 wherein the medical device comprises a transdermal applicator for medicinal fluids.

3. The combination of claim 2 wherein the transdermal applicator comprises a semipermeable membrane.

4. The combination of claim 3 wherein the adhesive adheres to at least a portion of said semipermeable membrane.

5. A combination as in claim 1 wherein the adhesive has a thickness of at least 0.7 mil and permits at least 90 percent of the adhesive surface of the transdermal device in contact with the skin to remain adhesive after 24 hours.

6. A combination as in claim 1 wherein the adhesive has a peel adhesion from stainless steel of at least 570 gm. per inch width.

7. A combination as in claim 1 wherein the weight ratio of methyl/phenyl polysiloxane to dimethylpolysiloxane comprises between about 1/3 to 3/1.

* * * * *